United States Patent [19]

Underwood et al.

[11] Patent Number: 5,756,035
[45] Date of Patent: May 26, 1998

[54] METHOD OF MAKING AN ACCESS GRAFT AND A VASCULAR PROSTHESIS

[75] Inventors: Christopher John Underwood, Manchester; David Charlesworth, Knutsford, both of England; Kerm Sin Chian, Singapore, Singapore

[73] Assignee: PolyMedica Industries, Inc., Woburn, Mass.

[21] Appl. No.: 655,317

[22] Filed: May 24, 1996

Related U.S. Application Data

[63] Continuation-in-part of Ser. No. 182,156, Apr. 29, 1994, abandoned.

[30] Foreign Application Priority Data

Aug. 1, 1991 [GB] United Kingdom ............... 9116563
Jul. 21, 1992 [WO] WIPO ............... PCT/GB92/01338

[51] Int. Cl.[6] ............................................. B29C 53/08
[52] U.S. Cl. ........................... 264/295; 264/306; 264/339
[58] Field of Search ............................ 264/295, 306, 264/339, 234

[56] References Cited

U.S. PATENT DOCUMENTS

| | | | |
|---|---|---|---|
| 2,964,796 | 12/1960 | Press | 264/339 |
| 4,257,422 | 3/1981 | Duncan | 128/350 R |
| 4,345,414 | 8/1982 | Bornat et al. | 264/234 |
| 4,562,597 | 1/1986 | Possis et al. | 623/1 |
| 4,888,074 | 12/1989 | Pocknell | 264/295 |
| 5,132,066 | 7/1992 | Charlesworth et al. | 264/184 |

FOREIGN PATENT DOCUMENTS

| | | |
|---|---|---|
| 55-51545 | 4/1980 | Japan ............... 264/306 |
| WO 84/02266 | 6/1984 | WIPO . |
| WO 89/01765 | 3/1989 | WIPO . |
| WO 91/05522 | 5/1991 | WIPO . |

*Primary Examiner*—Robert Davis
*Attorney, Agent, or Firm*—Oblon, Spivak, McClelland, Maier & Neustadt, P.C.

[57] ABSTRACT

A vascular prosthesis is adapted for use as an access graft having a permanent set, kink-resistant U-bend section. A method for making the access graft includes the utilization of a tube of implantable material adapted to be attached in a blood circulatory system and to provide thereby a site for access for cannulation, the tube having a permanent set, kink-resistant U-shaped bent section and the method including the steps of forming a straight tube by a process which yields a set, dryable tube; taking a length of the tube and inserting in it along its length a flexible rod-like support member; wrapping the tube containing the support member around a core so as to define a bend in the tube, the bend being wet at this stage; drying the wet tube containing the support member while wrapped around the core to permanently shape the tube into a bent form; removing the dried tube from the core and removing the support member so as to form an access graft, U-shaped bent section.

12 Claims, 3 Drawing Sheets

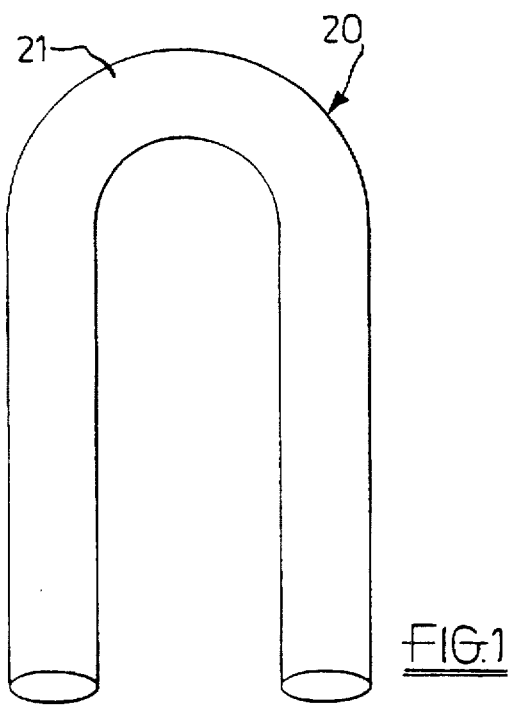
FIG. 1
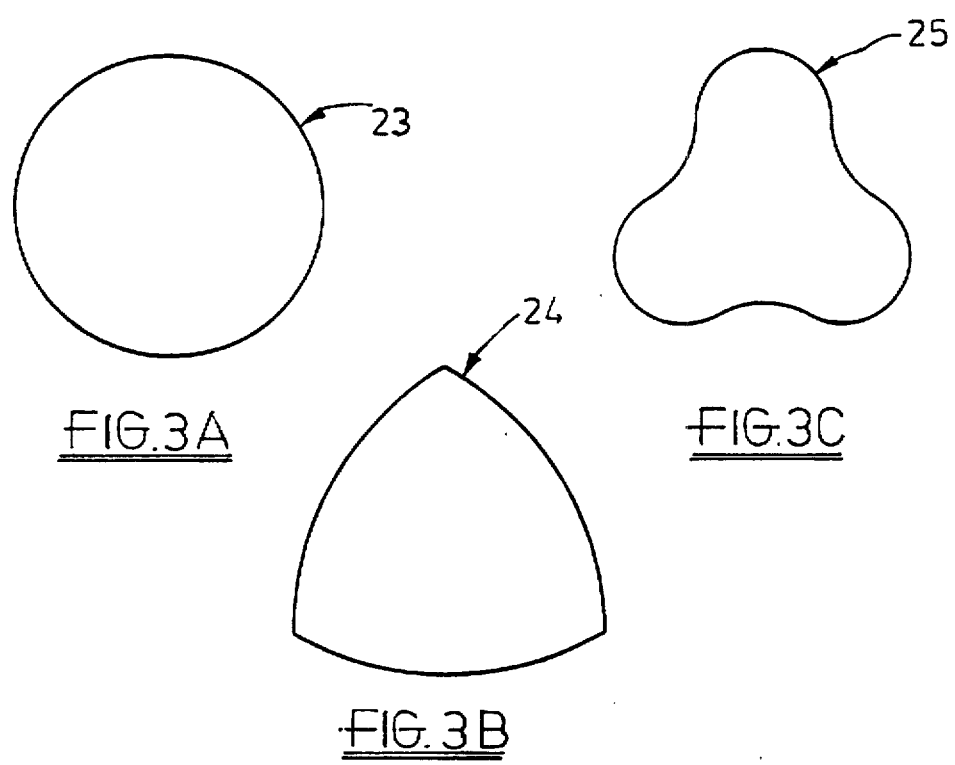
FIG. 3A
FIG. 3B
FIG. 3C

METHOD OF MAKING AN ACCESS GRAFT AND A VASCULAR PROSTHESIS

This is a continuation-in-part of application Ser. No. 08/182,156, filed Apr. 29, 1994, now abandoned, which was filed as PCT/GB92/01338 on Jul. 21, 1992.

BACKGROUND OF THE INVENTION

1. Technical Field

This invention concerns a vascular prosthesis adapted for use as an access graft, for example, for use in dialysis patients and also relates to molding an access graft, for example for use in dialysis patients and also relates to a method of making an access graft, for example for use by dialysis patients.

2. Background Art

At present, to make a vascular access graft, straight pieces of conventional artificial vascular prostheses, having circular cross-sections, are placed, usually, in the forearm of patients during surgery, and simply bent into a loop in situ. However, a major problem is that the artificial vessel may kink at the point where the vessel bends, and, because the vessel is circular, the lumen will totally occlude, thus interrupting normal blood flow. This problem may be overcome to some extent by having access grafts with thick walls and small internal diameters which are more kink resistant than those with thinner walls and larger internal diameters. However, if the walls of the graft are too thick and lumen too small, the graft will not only have a reduced compliance but also it will be very difficult to repeatedly introduce the large bore needle, i.e., 15 gauge, used for dialysis purposes.

It has been proposed to provide a vascular prosthesis adapted for use as an access graft which has a permanent set, kink-resistant U-shaped bent section. The U-shaped bent section is fashioned from a straight, flexible tubular graft which has been made for example by coagulation casting a bio-compatible polymer such as poly(ether)urethane and inserting a bend in the tube when wet, then drying the tube.

The achievement of high quality output of access grafts on this basis is problematical, however.

DISCLOSURE OF THE INVENTION

The present invention provides a vascular prosthesis for use as an access graft which overcomes, to some extent, the problems aforesaid.

According to the invention there is provided a vascular prosthesis adapted for use as an access graft which has a permanent set, kink-resistant U-shaped bent section.

The cross-section of the prosthesis may be circular or may be non-circular. Examples of non-circular cross-sections for prostheses are tricuspid, epitrochoid and deltoid cross-sections.

The vascular prosthesis may be arranged to be 'self sealing' after multiple needle punctures.

According to the invention there is also provided a method of making a vascular prosthesis which comprises the steps:

a) making a length of bio-compatible vascular prosthesis by coagulation casting and not allowing the casting to dry, then rewetting the casting, b) forming a U-shaped bent section in the prosthesis without introducing a kink therein, c) drying the prosthesis while so formed.

According to the invention there is also provided a method of making a vascular prosthesis which comprises the steps:

a) making a length of bio-compatible vascular prosthesis by coagulation casting and allowing the casing to dry, b) forming a U-shaped bent section in the prosthesis without introducing a kink therein, and c) drying the prosthesis while so formed.

The prosthesis may be made of a heat degradable polymer and then drying is effected at a temperature which will not degrade the polymer. However, drying may clearly be carried out at temperatures up to 40° C. (blood heat) as polymers which will degrade at such temperatures are obviously unsuitable for implantation.

A solution of coagulatable polymer may be dissolved in an organic solvent and may be coagulation cast onto a mandrel to make the prosthesis.

The mandrel may have a circular cross-section, or a non-circular cross-section. Examples of non-circular cross-sections are tricuspid, eiptrochoid and deltoid cross-sections.

The mandrel may be a pre-formed tube of PTFE and/or may be dip coated in the polymer solution.

The polymer solution may, however, be extruded through an extrusion head onto the mandrel to more easily provide a prosthesis of uniform wall thickness.

The polymer solution may contain a pore-forming agent soluble in a coagulant to leave a porous cast.

The polymer may comprise polyurethane, and may be a linear segmented poly(ether)urethane with an average molecular weight in the region 20,000 to 60,000.

The solvent may be aprotic, and may comprise N,N-dimethylacetamide or N,N-dimethylformamide. The concentration of the polymer in the solution may be between 10 and 30 grams/deciliter. The coagulant may comprise water.

The present invention also provides a method by which high quality access grafts can be produced to standard dimensions.

The invention comprises a method for making an access graft comprising a tube of implantable material adapted to be attached in a blood circulatory system and to provide thereby a site for access for cannulation, the tube having a permanent set, kink-resistant U-shaped bent section, the method comprising:

forming a straight tube by a process which yields a set, dryable tube;

taking a length of the tube and inserting in it along its length a flexible rod-like support member;

wrapping the tube containing the support member around a core so as to define a bend in the tube, the tube being wet at this stage;

drying the wet tube containing the support member while wrapped around the core to thereby permanently shape the tube into a bent form;

removing the dried tube from the core and removing the support member so as to form an access graft, U-shaped bent section.

The tube may, as before, be one that has been formed by coagulation coating on a former in the fashion described in WO 90/05628.

The tube may be allowed to dry after forming and is then re-wet before the wrapping step. Alternatively, the tube can be taken to the wrapping step without ever being allowed to dry.

The support member may be an easy sliding fit in the tube, but should be a reasonably snug fit—its purpose being to prevent kinking—consonant with insertion and removal—primarily insertion. The support member, to ease insertion, is preferably of or is coated with a silicone or like substance that does not stick to the tube. If the tube is wet for the insertion of the support member, it is found to have a useful lubricating effect.

The core may comprise a circular or near circular rod-like member having a diameter substantially the same as that of the tube—this provides an access graft of appropriate shape. The rod-like member may have helical fin means in which the tube is located. The eventual shape of the tube is found to depend on the extent of wrap and, for any particular material and configuration, it may be necessary to conduct a few trials with different extents of wrap necessary to produce the desired shape.

Typically, however, an appropriately shaped graft will be produced if the tube is wrapped twice around the core.

The wet tube wrapped on the core is constrained against movement (as by hanging weights on the protruding ends of the flexible support member) for drying—taking care not to deform the tube by excessive loading. Drying is preferably effected gently as by leaving the tube overnight in an oven at no more than 40° C.

BRIEF DESCRIPTION OF THE DRAWINGS

The invention will be further apparent from the following description with reference to the figures of the accompanying drawings, which show by way of example only, three forms of the vascular prosthesis embodying the same and from the method for making an access graft according to the present invention, in which:

FIG. 1 shows a top view of the prosthesis of the invention;

FIGS. 3A–3C show a cross-section of three types of mandrels to produce the prostheses of FIGS. 2A–2C.

BEST MODES FOR CARRYING OUT THE INVENTION

FIG. 1 shows a vascular prosthesis 20 adapted for use as an access graft having a permanent set, kink-resistant U-shaped bent section 21. As shown in FIG. 1, the section has a substantially constant cross-sectional shape throughout its length.

Figure 2A:
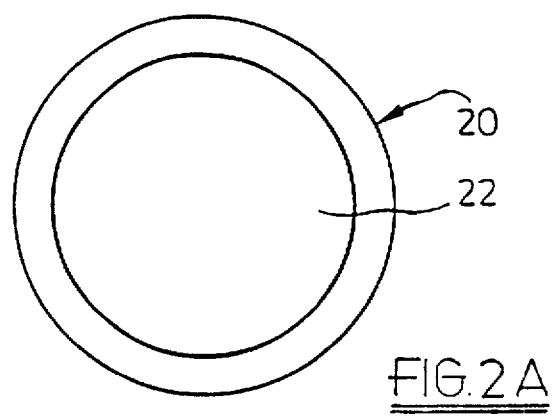
FIGS. 2A–2C shows a cross-section of three types of the prosthesis shown in FIG. 1.
Figure 2B:
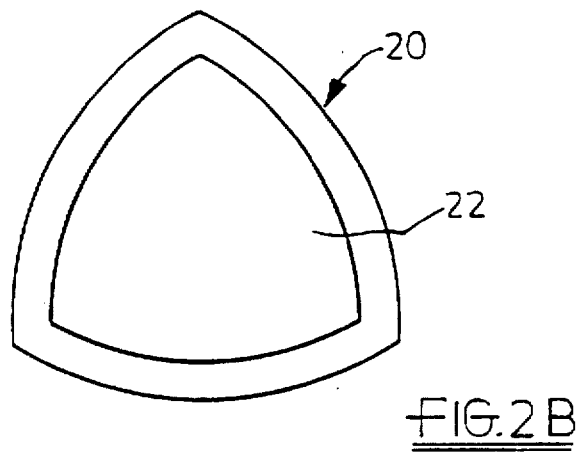
Figure 2C:
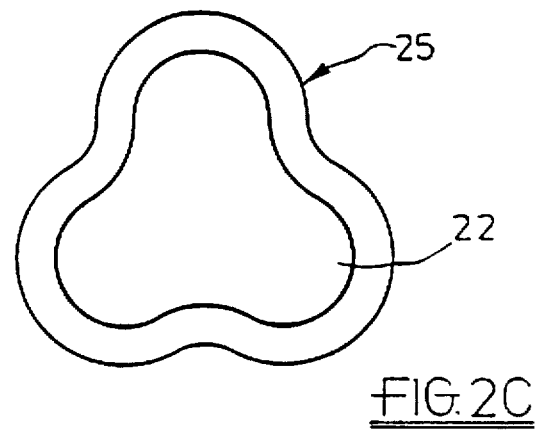
Figure 4:
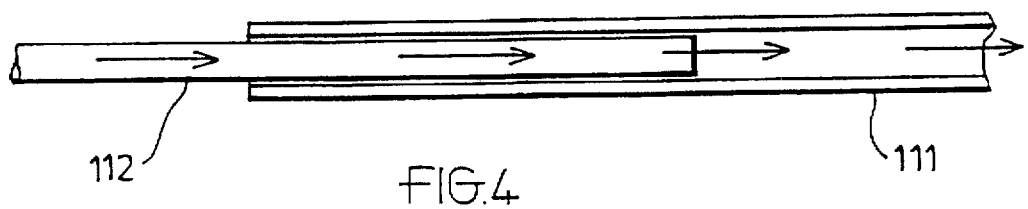
FIG. 4 is a drawing showing the insertion of a flexible rod-like support member in a coagulation-cast tubular prosthesis.
Figure 5:
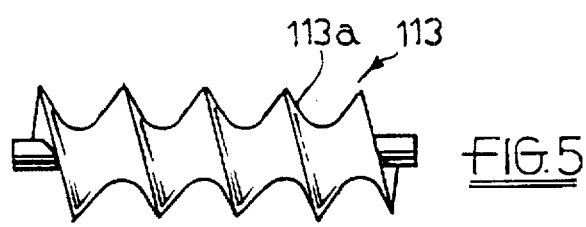
FIG. 5 is an elevational view of a core on which the tube can be wrapped.

The cross-sectional shape of the prosthesis 20 is not limited. FIGS. 2A–2C show three cross-sections of the prosthesis 20, a circular cross-section in FIG. 2A, a tricuspid epitrochoid cross-section in FIG. 2B and a deltoid cross-section in FIG. 2C. The prosthesis 20 may have a non-circular cross-section, whereof the lumen 22 will not totally occlude, thus further increasing the kink-resistance of prosthesis 20.

The prosthesis 20, is made from a bio-compatible material, such as an elastomer, or a combination of elastomer and polytetrafluoroethylene (PTFE). Preferred elastomers include polyurethane, polyurethaneurea, segmented polyurethanes and segmented polyurethaneureas. These materials give the prosthesis 20 the property of tending to be 'self-sealing' after needle puncture, even after multiple needle punctures.

The prosthesis 20 has a wall thickness and lumen size capable of withstanding multiple needle puncture by a large bore, i.e., 15 gauge needle used for dialysis treatment, while maintaining a compliance similar to that of natural vessels, overcoming the problem which at present prevents such thicker walled, small diameter conventional prostheses being used as access grafts.

The prostheses 20, having a permanent set, kink-resistant U-shaped bent section 21 is made from a length of vascular prosthesis by coagulation casting a solution of coagulatable heat degradable polymer dissolved in an organic solvent onto a mandrel. Before allowing the casting to dry, or after re-wetting the casting after drying, a U-shaped bent section is formed in the prosthesis without introducing any kinks therein, and the prosthesis so formed is dried.

The prosthesis 20 is dried in an oven at a temperature which will not degrade the polymer, usually up to 40° C.

The U-shaped bent section 21 is formed in the length of prosthesis, after the introduction of an internal flexible former to prevent collapse of the lumen of the prosthesis on bending, either by drying over a shaped former, or by simply bending the length of prosthesis, having locating means to maintain the U-shaped bent section in position until dried. Once dried the internal flexible former is removed.

A solution of coagulatable polymer, such as a linear segmented polyetherurethane with an average weight of 20,000 to 60,000, is dissolved in a solution comprising an organic solvent, such as N,N-dimethylacetamide or N,N-dimethylformamide, at a concentration of polymer in a solution of between 20 and 30 grams/deciliter.

In addition, the polymer solution contains a pore-forming agent, soluble in a coagulant to leave a porous cast, such as sodium hydrogen carbonate ground to an average particle size of 60 microns in an amount between 10 and 60 percent by weight.

The polymer solution also contains a surfactant, such as sodium dodecyl sulphate, in an amount between 1 and 10 percent by weight.

A length of prosthesis is produced either by dip coating a mandrel in the polymer solution, or, to more easily produce a prosthesis having a uniform wall thickness, by extruding the polymer solution through an extrusion head as described in GB-A-2,204,873, the disclosure of which is incorporated herein by reference. The polymer-coated material is then immersed in a coagulant and allowed to coagulate.

The preferred coagulant is water which is maintained at a constant temperature throughout the coagulation process, usually 40° C. The coagulation process normally takes 1 to 2 hours.

The mandrel is not limited in its cross-section. FIGS. 3A–3C shows three examples of mandrels. Mandrel 23 has a circular cross-section and is used to produce the posthesis of FIG. 2A. Mandrel 24 has a tricuspid epitrochoid cross-section and is used to produce the prosthesis of FIG. 2B. Mandres 25 has a deltoid cross-section and is used to produce the prosthesis of FIG. 2C.

Figure 7:
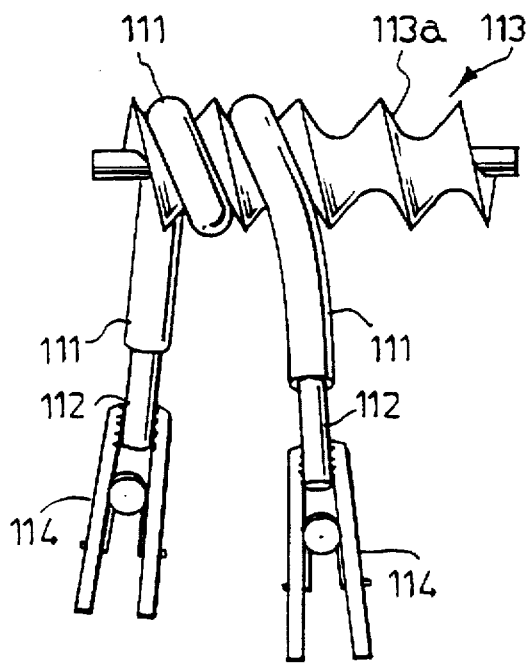
FIG. 7 is an elevational view of the resulting graft from the method of making an access graft.
Figure 6:
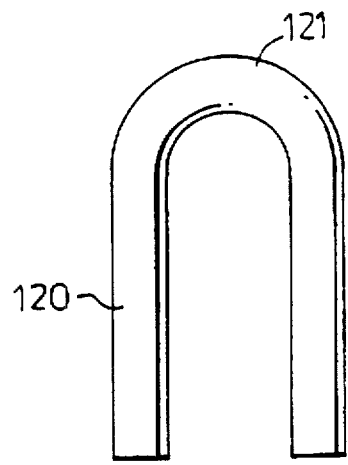
FIG. 6 is an elevational view showing the tube in place on the core.

The drawings of FIGS. 4–7 illustrate a method for making an access graft 120 (FIG. 7) comprising a tube of implantable material such as a poly(ether)urethane made as described in WO 90/05628, the disclosure of which is incorporated herein by reference, adapted to be attached in a blood circulatory system and to provide thereby a site 121 for access to cannulation and the tube having a permanent set, kink-resistant U-bend section (the site 121), the method comprising:

forming a straight tube 20 by a process (such as that described in WO 90/05628) which yields a wet, dryable tube;

taking a length 111 (FIG. 4) of the tube and inserting in it along its length a flexible rod-like support member 112;

wrapping the tube 111 containing the member 112 around a core 113 so as to define a bend in the wet tube—the tube 111 being wet at this stage;

drying the wet tube 111 containing the support member 112 while wrapped around the core 113 so as to permanently shape the tube 111 into a bent form;

removing the dried tube 111 from the core 113 and removing the support member 112 so as to form an access graft U-bend section as shown in FIG. 7.

The tube 111 may be allowed to dry after being cast according to WO 90/05628 and may be processed dry up to an including its wrapping on the core 113, when it is wetted. However, if the manufacture of access grafts takes place reasonably close in time and space to the initial production of the tube 111, the later may be taken wet straight from the casting process and never allowed to dry up to and including it being wrapped on the core 113. It is found that the presence of water aids the insertion of the rod-like member 112 and a dry tube 111 might be wetted-out prior to such insertion.

The member 112 should be a reasonably snug fit in the tube 111, but not such as to render threading-on too difficult. Being of or coated with silicone or like material helps insertion and removal.

The core 113 comprises a circular or near circular rod-like member having a diameter substantially the same as that of the tube 111. There is a helical fin 113a in which, as see in FIG. 6, the tube (with its insert member 112) is located while wrapped (twice in this case) around the core 113.

After wrapping on the core 113 (either already wet, or dry, and then wetted-out) the tube 111 is placed in an oven overnight at 40° C. (not more, or at least not substantially more) to dry out so as to set the tube 111 so that, on removal from the core 113 and after retrieval of the support member 112, it constitutes a tube 120 with a U-shaped bent section 121.

The wet (and drying) graft wrapped on the core 113 is constrained against movement by hanging weights 114 (or weighted clasps) whose weights are respectively not such as to cause deformation of the graft, and dried overnight at 40° C.

It will be appreciated that it is not intended to limit the invention to the above example only, many variations, such as might readily occur to one skilled in the art, being possible, without departing from the scope thereof as defined by the appended claims.

We claim:

1. A method for making an access graft comprising a tube of implantable material adapted to be attached in a blood circulatory system and to provide thereby a site for access for cannulation, the tube having a permanent set, kink-resistant U-bend section, the method comprising:

forming a straight tube by a process which yields a set, dryable tube;

taking a length of the tube and inserting in the tube along a length of the tube a flexible rod-like support member at least twice;

wrapping the tube containing the support member around a core so as to define a bent section in the tube while the tube is wet;

drying the wet tube containing the support member while wrapped around the core and shaping the tube into a bent form;

removing the dried tube from the core and removing the support member so as to form an access graft, U-shaped section.

2. A method according to claim 1, which comprises forming the tube by coagulation casting on a former.

3. A method according to claim 2, which comprises drying after forming and rewetting the tube before the wrapping step.

4. A method according to claim 2, which comprises preventing the tube from drying between the forming of the tube and wrapping the tube.

5. A method according to claim 1, which comprises slidably fitting the support in the tube when inserting the support member in the tube.

6. A method according to claim 5, wherein the support member comprises one of a silicone coated member and a member coated with a silicone-like substance that does not stick to the tube.

7. A method according to claim 1, wherein the core comprises one of a circular and a substantially circular rod-like member having a diameter substantially the same as that of the tube.

8. A method according to claim 7, wherein the rod-like member has a helical fin in which the tube is located.

9. A method according to claim 8, wherein the wrapping of the tube comprises wrapping the tube twice around the rod-like member.

10. A method according to claim 1, which comprises constraining the wrapped, wet tube on the core against movement for drying.

11. A method according to claim 1, which comprises drying the tube in an oven at a temperature not exceeding 40° C.

12. A method as claimed in claim 10, which comprises hanging a weight to opposite ends of the wet tube so as to constrain the wet tube against movement on the core.

* * * * *

UNITED STATES PATENT AND TRADEMARK OFFICE
CERTIFICATE OF CORRECTION

PATENT NO. : 5,756,035
DATED : May 26, 1998
INVENTOR(S) : Christopher J. Underwood et al.

It is certified that error appears in the above-identified patent and that said Letters Patent is hereby corrected as shown below:

Column 6,
Line 11, after member delete "at least twice" and
Line 13, after "core" insert -- at least twice --.

Signed and Sealed this

Twentieth Day of January, 2004

JON W. DUDAS
*Acting Director of the United States Patent and Trademark Office*